United States Patent
Costa

(10) Patent No.: US 9,347,083 B2
(45) Date of Patent: May 24, 2016

(54) CULTURE MEDIUM CONTAINING A SPORE GERMINATION INHIBITING OR DELAYING COMPOUND

(75) Inventor: Aurelien Costa, Grenoble (FR)

(73) Assignee: BIOMERIEUX, Marcy l'Etoile (FR)

( * ) Notice: Subject to any disclaimer, the term of this patent is extended or adjusted under 35 U.S.C. 154(b) by 480 days.

(21) Appl. No.: 12/995,498

(22) PCT Filed: Jun. 23, 2009

(86) PCT No.: PCT/FR2009/051201
§ 371 (c)(1),
(2), (4) Date: Dec. 1, 2010

(87) PCT Pub. No.: WO2010/004164
PCT Pub. Date: Jan. 14, 2010

(65) Prior Publication Data
US 2011/0076717 A1  Mar. 31, 2011

(30) Foreign Application Priority Data
Jun. 26, 2008 (FR) ...................... 08 54275

(51) Int. Cl.
  *C12Q 1/14* (2006.01)
  *C12Q 1/04* (2006.01)
(52) U.S. Cl.
  CPC . *C12Q 1/045* (2013.01); *C12Q 1/14* (2013.01)
(58) Field of Classification Search
  None
  See application file for complete search history.

(56) References Cited

U.S. PATENT DOCUMENTS

| | | | |
|---|---|---|---|
| 6,063,590 A | 5/2000 | Brenner et al. | |
| 6,617,126 B1* | 9/2003 | Horn | C12Q 1/045 435/244 |
| 7,235,379 B2* | 6/2007 | Roger-Dalbert | 435/34 |
| 7,754,485 B2* | 7/2010 | Kocagoz | C12N 1/20 435/243 |
| 7,807,439 B2* | 10/2010 | Cotte et al. | 435/243 |
| 2004/0121404 A1 | 6/2004 | Cotte et al. | |

FOREIGN PATENT DOCUMENTS

| | | |
|---|---|---|
| EP | 1 390 524 B1 | 10/2006 |
| EP | 1 873 256 A2 | 1/2008 |

OTHER PUBLICATIONS

Ferencko et al. "Esterase activity as a novel parameter of spore germination in Bacillus anthracis". Biochemical and Biophysical Research Communications. 2004, 319, pp. 854-858.*
Casaburi et al. "Protease and esterase activity of staphylococci". International Journal of Food Microbiology. 2006, vol. 112, No. 3, pp. 223-229.*
Boschwitz et al. Journal of General Microbiology 1991, 137, pp. 1145-1153.*
Atlas R. Handbook of Microbiological Media. CRC Press. 1993, pp. 112, 113, 254, 255, 720, 721, 918, 919, 949 and 950.*
Finegold et al. Journal of Bacteriology. 1961, vol. 81, pp. 636-641.*
M. Halmann et al.; "Stages in Germination of Spores of *Bacillus Licheniformis*;" *J. Bacteriol.*; vol. 84; pp. 1187-1193; Jul. 13, 1962.
Y. Yasuda-Yasaki et al.; "Inhibition of *Bacillus subtilis* Spore Germination by Various Hydrophobic Compounds: Demonstration of Hydrophobic Character of the $_L$-Alanine Receptor Site," *J. Bacteriol.*; vol. 136, No. 2; pp. 484-490; Nov. 1978.
Y. Yasuda et al.; "Regulation of L-alanine-initiated germination of Bacillus subtilis spores by alanine racemase;" *Amino Acids*; vol. 4, No. 1-2; pp. 89-99; Feb. 1993.

* cited by examiner

*Primary Examiner* — Vera Afremova
(74) *Attorney, Agent, or Firm* — Oliff PLC

(57) ABSTRACT

A medium for the culture and detection of target microorganisms, having at least one natural or synthetic specific substrate configured to detect at least one enzyme activity or metabolic activity of the target microorganisms and at least one compound that inhibits or delays the germination of spores of microorganisms, other than the target microorganisms, that are capable of interfering with the culture and detection of the target microorganisms.

20 Claims, 1 Drawing Sheet

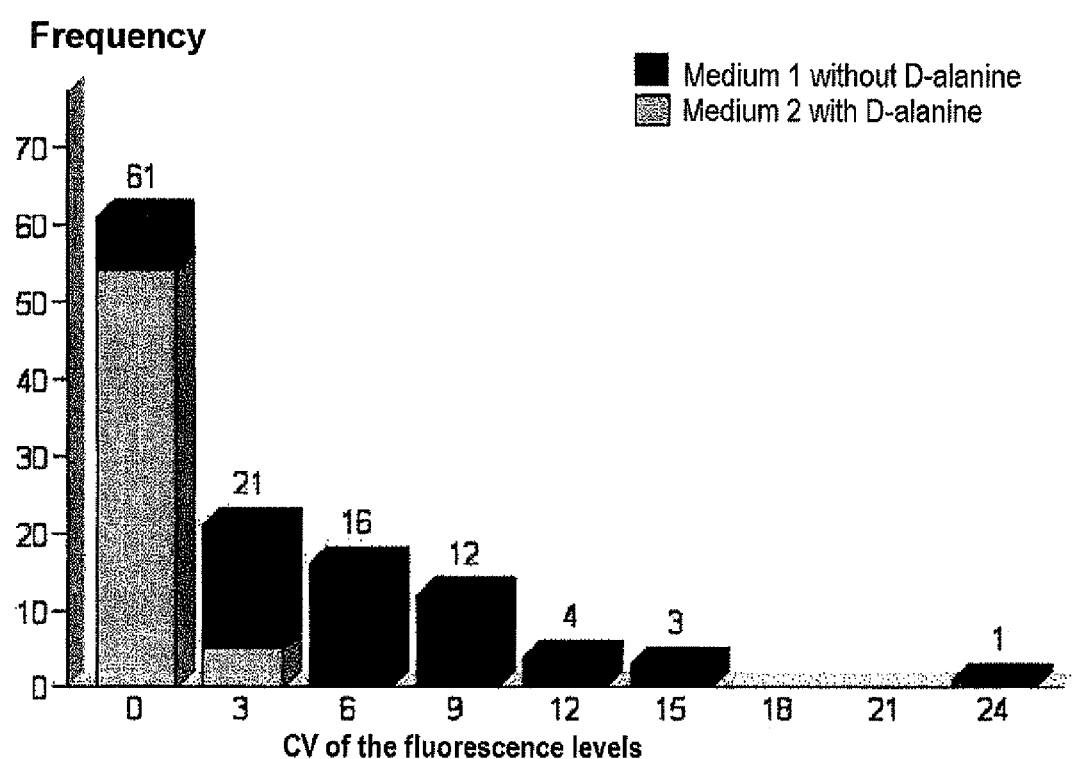

ns which, as
CULTURE MEDIUM CONTAINING A SPORE GERMINATION INHIBITING OR DELAYING COMPOUND The field of the invention is that of clinical or industrial microbiological testing. More particularly, the present invention relates essentially to a medium for the culture of target microorganisms which may be present in a sample, more particularly in a food or environmental sample, said culture medium containing at least one spore germination inhibiting or delaying compound.

The present invention will be particularly described hereinafter with reference to dehydrated products, without this constituting, however, a limitation to the invention.

Quality and safety are the major preoccupations of the food-processing industry throughout the world. It must be possible to detect, identify and quantify the microbial flora in the starting materials and the final products, and thus to guarantee the value of the products, from their production to their consumption. Product quality indicators are thus analyzed, reflecting an overall level of contamination with a modifying flora, among which are enterobacteria such as *Escherichia coli*, coagulase-positive staphylococci, *Pseudomonas, Bacillus*, yeasts, molds, etc. In particular, searching for coagulase-positive staphylococci in milk powders has today become imperative.

Among coagulase-positive staphylococci, *Staphylococcus aureus* is the most pathogenic species of the *Staphylococcus* genus, although it is commensal in humans. Specifically, it can be responsible for food poisoning, for suppurative localized infections and, in certain extreme cases, septicemia in individuals who have undergone a transplant or who have a cardiac prosthesis.

The difficulty in developing a culture medium allowing the specific counting of coagulase-positive staphylococci lies:
  not only in the need for this culture medium to have good sensitivity, allowing the detection of a very low contamination of coagulase-positive staphylococci (about 10 colony forming units (CFU)/g) present in said medium, but also
  in the need to be able to inhibit levels, which are sometimes very high, of other microorganisms, and most particularly of microorganisms such as *Bacillus* microorganisms which are phenotypically close to coagulase-positive staphylococci.

This is because, as regards in fact the *Bacillus* microorganisms, differentiating between coagulase-positive staphylococci and *Bacillus* by means of selective agents is found to be particularly difficult; most of the inhibitors which are effective on one of these bacteria generally also affect the other bacterium. Thus, it has been observed that conventional culture medium of the Baird-Parker-RPF (rabbit plasma+bovine fibrinogen) type does not allow effective and systematic inhibition of *Bacillus*.

Moreover, in the food-processing field, manufacturers often have recourse to processes for producing products by dehydration, the conditions of which generally make it possible to eliminate most of the microorganisms, in particular in their vegetative form. However, bacteria of the *Bacillus* genus, owing to their ability to form spores, are capable of withstanding extreme conditions such as those used during dehydration. They are then found in the dehydrated products. Thus, it has been observed that the level of *Bacillus* contamination in powdered milks can be high.

Furthermore, most of the starting materials required for preparing culture media are themselves also frequently in dehydrated (powder) form.

These dry starting materials are also regularly contaminated with these *Bacillus* microorganisms which, as explained above, withstand the dehydration conditions.

Consequently, false-positive results are frequently observed in the microbiological testing of dehydrated products such as milk powders, owing to the fact that bacteria of the *Bacillus* genus are analyzed, wrongly, as being coagulase-positive staphylococci.

Conversely, the risk of false negatives is just as high since the often large amount of *Bacillus*, which is always much higher than that of the coagulase-positive staphylococci, often masks the presence of the latter.

It can therefore be easily understood that a large amount of *Bacillus* proves to be a major obstacle to the development of a culture medium intended for identifying, or even counting, target bacteria such as coagulase-positive staphylococci and can result in a poor estimation of the presence of these microorganisms present in an analytical sample such as a food sample. The sample is defined as a small part or a small amount isolated from an entity for analysis.

Although various methods for developing a culture medium for the purpose of the specific counting of coagulase-positive staphylococci have been tested, they have not resulted in the expected success, with regard to limitation of the impact of *Bacillus*.

Thus, selective agents such as antibiotics do not make it possible to combine good selectivity with respect to *Bacillus* microorganisms with maintaining good sensitivity with respect to coagulase-positive *staphylococcus* microorganisms.

Two publications going back several tens of years referred to the action of D-alanine on spore germination.

Thus, it is known from the publication by M. Halmann, A. Keynan, 1962, "Stages in germination of spores of *Bacillus Licheniformis*", J. Bacteriol. 84: 1187-1193, that L-alanine dehydrogenase is necessary for the first biochemical step of *Bacillus licheniformis* spore germination and that this first step can be inhibited with D-alanine, various salts, ethyl pyruvate and octanol.

It is also mentioned in the publication by Yoko Yasusa-Yasaki et al., 1978, "Inhibition of *Bacillus subtilis* Spore Germination by Various Hydrophobic Compounds: Demonstration of Hydrophobic Character of L-alanine Receptor Site", Journal of Bacteriology, Vol. 136, No 2, p. 484-490, that the inhibitors of L-alanine responsible for the initiation of sporulation are:
  octanol on *Bacillus licheniformis* and *Bacillus cereus*,
  phenylethyl alcohol on *Bacillus megaterium*,
  8-hydroxyquinoline on *Bacillus megaterium, Bacillus cereus* and *Bacillus subtilis*,
  ethanol and dicyclohexylcarbodiimide on *Bacillus cereus*.

The studies subsequently published focus essentially on characterizing the mechanism of germination of the sporulated forms of the microorganisms, of which the *Bacillus* genus is an example.

Said studies in fact describe the various steps which are involved in the germination process.

This knowledge of the germination mechanism was up until now essentially used to promote the germination of microorganism spores, in particular *Bacillus* spores, with several objectives:
  accelerating germination and thus improving growth/detection in culture media;
  promoting germination in order to eliminate the microorganisms in their vegetative form, which are then much more sensitive to the inhibiting agents present in the form of antibiotics in the culture media or in the form of detergents or disinfectants in certain industrial cleaning processes, other processes being, for their part, based on high-temperature treatments.

The present invention proposes to remedy the abovementioned drawbacks by providing a solution which goes against those already identified and which consist not in promoting spore germination, but, on the contrary, in blocking it or, at the very least, delaying it.

It represents, moreover, an entirely advantageous alternative to the use of antibiotics, the spectra of action of which are not generally compatible with the need to differentiate between the target microorganisms such as coagulase-positive staphylococci and microorganisms, such as *Bacillus*, capable of interfering in the detection, identification or even counting of said target microorganisms.

The present invention also has the advantage of not modifying the nutritive qualities of the culture medium, thereby making it possible to avoid the problems of specificity mentioned above and to thus make the developed culture medium more particularly suitable for the analysis of products such as dehydrated products, in which the level of *Bacillus* is high.

Consequently, one of the essential objectives of the present invention consisted in using a medium for the culture of target microorganisms, in particular of bacteria, which is capable of blocking, or at the very least delaying, the germination of spores possibly contained in the sample to be analyzed, without this having an effect on the growth of said target microorganisms.

A first subject of the invention thus consists of a medium for the culture and detection of target microorganisms, comprising:
- at least one natural or synthetic specific substrate allowing the detection of at least one enzyme activity or metabolic activity of said target microorganisms,
- at least one compound inhibiting or delaying the germination of spores of microorganisms, other than the target microorganisms, which are capable of interfering with the culture and detection of said target microorganisms.

Preferably, the target microorganisms are bacteria, among which are coagulase-positive staphylococci, including *Staphylococcus aureus*.

For the purpose of the present invention, the substrate may be a metabolic substrate, such as a carbon or nitrogen source, the degradation product of which causes the pH to vary, said variation being detectable by means of a pH indicator. The pH indicator is a chemical substance of which the color varies according to changes in pH associated with microbial growth. Mention will be made, as examples of chromophores, of neutral red, aniline blue and bromocresol blue. In a second embodiment, the pH indicator is a fluorophore (for example, 4-methylumbelliferone, aminocoumarin derivatives or resorufin derivatives).

The substrate may also be chosen from any substrate that can be hydrolyzed to give a product which allows the direct or indirect detection of an enzyme activity specific for the microorganism being sought. In the case of direct detection, the substrate comprises a first part specific for the enzyme activity and a second part that acts as a label, which may be chromogenic or fluorescent.

The culture medium which is the subject of the invention may be in the form of a powder, in the form of a gel or in the form of a liquid, which is ready to use, i.e. ready for inoculation in a tube or a flask or on a Petri dish. In the case of a gel medium, agar is the conventional gelling agent in microbiology for the culture of microorganisms, but it is possible to use gelatin or agarose. Finally, the medium may be packaged in a bottle, a cartridge or a card, specific for an automated bacteriological instrument (by way of example, mention will be made of the Vitek® card, the Tempo® card and the BacT/ALERT® bottle, which are sold by the applicant). In this case, the delaying or inhibiting compound may be in the form of an independent solution intended to be added to the culture medium before its use.

Among the samples of food origin, mention may be made, non-exhaustively, of a sample of dehydrated products such as milk powders, cereals, soup powders or cake preparations. This is also the case of pastries. Finally, a food sample can be derived from an animal feed, such as, in particular, animal meals.

Mention will also be made of samples related to the environment, such as surface specimens, water specimens or air specimens.

In one preferred embodiment of the invention, said inhibiting or delaying compound inhibits or delays the germination of *Bacillus* spores.

The spore germination inhibiting or delaying compound is advantageously chosen from the group comprising D-alanine, diphenylamine, alcohols of formula $C_nH_{2n+2}OH$ where n ranges from 6 to 12, preferably octanol, nonanol or decanol, inhibitors of enzymes of trypsin type, and/or mixtures thereof.

According to one preferred embodiment, the concentration of the spore germination inhibiting or delaying compound in said medium is between 0.01 and 1 mol/l, preferably 0.05 and 0.1 mol/l.

The culture medium may also contain a pH indicator for revealing the consumption of the substrate, said pH indicator preferably being a chromophore or a fluorophore.

Conventionally, the substrate may comprise a first part specific for the enzyme activity or metabolic activity to be revealed and a second part that acts as a fluorescent label.

Alternatively, the substrate may comprise a first part specific for the enzyme activity or metabolic activity to be revealed and a second part that acts as a chromogenic label.

A second subject of the present invention relates to a method for the detection of target microorganisms which may be present in a sample, comprising the steps consisting in:
a) bringing said sample into contact with a culture medium according to the invention,
b) incubating said culture medium under conditions suitable for microorganism cell multiplication,
c) detecting the presence of said target microorganisms.

According to one particular embodiment, the method according to the invention can comprise a step prior to step a), which consists in adding, to said culture medium, a solution containing at least one compound inhibiting or delaying the germination of spores of microorganisms, other than the target microorganisms, which are capable of interfering with the culture and detection of said target microorganisms.

Step c) of the method according to the invention can consist in measuring the variation in the level of fluorescence in the culture medium using a fluorescence reader, this variation corresponding, for example, to a variation in the pH in said culture medium.

Alternatively, step c) can consist in identifying the colonies. In this case, the culture medium according to the invention is typically in solid form, in particular in the form of agar medium in Petri dishes. Since the spore germination is delayed, the bacteria of interest grown as a priority over the other bacteria, and prior to the other bacteria, on the culture medium. Thus, in the case of early reading of the Petri dishes (16 hours after inoculation, for example), only the colonies of the bacteria of interest can be visible. In the case of later reading (24 hours after inoculation, for example), said reading consists in distinguishing the large colonies from the small colonies. The colonies of bacteria obtained by spore germination are smaller in size than those of the target bacteria which, themselves, have developed normally. It is then easy to distinguish between the target bacteria and the other bacteria.

According to one particular embodiment, the method according to the invention can comprise an additional step of counting target microorganisms. Such a counting step is preferably carried out according to the most probable number (MPN) method. This method is explained in patent EP 1 105 457 in the name of the applicant.

Another subject of the present invention relates to the use of at least one compound delaying or inhibiting the germination of microorganism spores, for the preparation of a culture medium.

Entirely preferably, the invention relates to the use of D-alanine for the preparation of a culture medium intended for identifying coagulase-positive staphylococci such as *Staphylococcus aureus*.

A final subject of the invention relates to the use of a culture medium for the detection, identification or even counting of coagulase-positive staphylococci.

The preparation of the culture medium according to the invention has the advantage of being completely compatible with the conventional conditions of methods for producing culture media, given that the spore germination inhibiting or delaying compounds are generally stable within a large range of temperature values, unlike antibiotics. Moreover, these compounds often have a low cost price.

The aims and advantages of the present invention will be understood more clearly in light of the example which follows, together with the drawing, in which:

FIG. 1 is a histogram graph showing the distribution of the CVs relative to the levels of fluorescence obtained after incubation with samples tested on culture medium with and without D-alanine.

EXAMPLE

The example described hereinafter illustrates the inhibiting effect of D-alanine on the sporulation of microorganisms of *Bacillus* type (such as *Bacillus licheniformis, Bacillus thuringiensis/cereus*).

To do this, 59 samples of milk powder products liable to contain *Bacillus* microorganisms, also not contaminated with *Staphylococcus aureus*, were tested.

In order to study the inhibiting effect of D-alanine, two culture media were tested:
  Medium 1: culture medium without D-alanine,
  Medium 2: culture medium in the presence of D-alanine at a final concentration in the medium of between 0.05 and 0.1 mol/l (final concentration in the medium).

The composition of said culture medium is the following (in g/l, final concentration in the medium with or without D-alanine):

| | |
|---|---|
| Animal (bovine and porcine) and plant peptones | 12.5 |
| Sugars and growth supplements | 11 |
| Buffer system | 10 |
| Selective agents (antibiotics, salts) | 10.25 |
| Fluorescent pH indicator | 0.06 |
| Antifoam | 0.4 |

The samples were prepared according to ISO standard 8261: 2001 (concerning milk and milk products and relating to the "general guidelines for the preparation of test samples, of the stock suspension and of the decimal dilutions for the purpose of microbiological examination") according to the following steps:

a) 10 grams of the sample are weighed out and placed in a Stomacher® bag, b) 90 ml of tryptone salt diluent preheated to 45° C. are added so as to obtain an initial 1/10 dilution of the sample, c) grinding is carried out using a Stomacher® machine for one minute, d) the Stomacher® bag is placed in a water bath and stirred for 5 minutes at 45° C., e) 1 ml of the sample (diluted to 1/10) is taken and placed in 3 ml of culture medium so as to obtain a 1/40 dilution, f) incubation is carried out for a period of between 24 and 27 hours at a temperature of 37° C., g) the culture medium is read by fluorescence and the level of contamination of the sample with microorganisms is determined by means of the most probable number technique.

The reading consists of a measurement of the fluorescence of the culture medium obtained after incubation. A large variation in the fluorescence values attests to acidification of the medium, said acidification itself resulting from the growth of one or more microorganisms.

The CV fluorescence values were calculated on the basis of the samples tested (not contaminated with *Staphylococcus aureus*).

The higher the CV, the greater the acidification of the medium, thereby attesting to growth of the microorganisms present in the culture medium. Conversely, the lower the CV, the less the acidification, thereby reflecting less growth of the microorganisms. The specificity of the medium is therefore better and the risk of false positives is therefore less (false-positive result linked to the acidification of the medium by a bacterium of a microorganism other than *Staphylococcus aureus*).

Since the samples tested in this example are not contaminated with *Staphylococcus aureus*, the acidifications observed are related to the nonspecific growth of various microorganisms other than *Staphylococcus aureus*, identified as belonging to the *Bacillus* genus (*Bacillus licheniformis, Bacillus thuringiensis/cereus*).

The profiles obtained and presented in the form of histograms, as represented in FIG. 1, show a considerable difference in the distribution of the CVs between the two culture media:

The CVs obtained with medium 1 (without D-alanine) are distributed over values between 0 and 24, whereas all the values obtained with medium 2 (with D-alanine) are less than 6 and the vast majority are less than 3 (very slight acidification).

The use of D-alanine in the culture medium makes it possible to greatly reduce the CV values obtained after incubation of the medium. Since the CVs are, in the case studied, related to nonspecific acidifications, the addition of D-alanine to the medium confers on said medium a better specificity with respect to *Bacillus* present on this type of sample in sporulated form.

Table 1 below recapitulates the counts obtained with or without D-alanine in the culture medium.

TABLE 1

| | D-alanine tested | | | |
| | Medium 1 | | Medium 2 | |
| MPN Count | % | N | % | N |
| --- | --- | --- | --- | --- |
| <10 | 50.85 | 30 | 89.83 | 53 |
| 10 < count < 50 | 42.37 | 25 | 10.17 | 6 |
| 50 < count < 100 | 6.78 | 4 | 0.00 | 0 |
| All | 100.00 | 59 | 100.00 | 59 |

With MPN: most probable number

It is noted that, among the 59 samples tested, medium 1 maintained good specificity in 50.85% of the count results obtained (MPN<10). 49.15% of the results are false positives and related to the growth of *Bacillus*, including 6.78% giving count results above 50 CFU/g.

The addition of D-alanine to the medium made it possible to improve the rate of <10 results from 50.85% to 89.83%. The rate of false-positive results was then reduced from 49.15% to 10.17%, and no false-positive result obtained exceeds 50 CFU/gram with the use of D-alanine.

The invention claimed is:

1. A liquid medium for the culture and detection of coagulase-positive staphylococci, comprising:
   peptones;
   at least one metabolic substrate capable of being degraded by a metabolic activity of the coagulase-positive staphylococci to cause the pH of the medium to vary;
   a pH indicator capable of detecting pH variation of the medium due to degradation of the metabolic substrate, the pH indicator being a chromophore or fluorophore; and
   D-alanine in an amount from 0.05 mol/L to 1 mol/L in the liquid culture medium.

2. The culture medium as claimed in claim 1, wherein the pH indicator is a chromophore.

3. The culture medium as claimed in claim 1, wherein the pH indicator is a fluorophore.

4. A method for determining whether coagulase-positive staphylococci are present in a sample, comprising:
   a) bringing said sample into contact with a liquid culture medium as claimed in claim 1,
   b) incubating said culture medium under conditions suitable for growth of the coagulase-positive staphylococci, and
   c) detecting whether the coagulase-positive staphylococci are present in the culture medium in order to determine whether the coagulase-positive staphylococci were present in the sample.

5. The method as claimed in claim 4, further comprising:
   adding to said culture medium, prior to step a), a solution containing D-alanine so that D-alanine is present in the culture medium in step a).

6. The method as claimed in claim 4, wherein step c) comprises measuring a variation in the level of fluorescence in the culture medium using a fluorescence reader, the variation corresponding to a variation in the pH in said culture medium.

7. The method as claimed in claim 4, wherein the sample is a food or environmental sample.

8. The method as claimed in claim 4, further comprising counting the coagulase-positive staphylococci.

9. A method of preparing a liquid culture medium, the method comprising:
   mixing together in a liquid medium:
   peptones;
   at least one metabolic substrate capable of being degraded by a metabolic activity of coagulase-positive staphylococci to cause the pH of the medium to vary;
   a pH indicator capable of detecting pH variation of the medium due to degradation of the metabolic substrate, the pH indicator being a chromophore or fluorophore; and
   D-alanine so that D-alanine is in an amount from 0.05 mol/L to 1 mol/L in the liquid culture medium.

10. The culture medium as claimed in claim 1, wherein the amount of D-alanine in the culture medium is from 0.05 mol/L to 0.1 mol/L.

11. The culture medium as claimed in claim 1, wherein the culture medium has a sensitivity of at least 10 colony forming units per gram (CFU/g) for the detection of the coagulase-positive staphylococci.

12. The culture medium as claimed in claim 1, wherein the peptones are animal and plant peptones.

13. The culture medium as claimed in claim 1, further comprising selective agents that permit the growth of the coagulase-positive staphylococci under culture conditions when present in a sample contacted with the medium.

14. The culture medium as claimed in claim 13, further comprising growth supplements and a buffer system.

15. The culture medium as claimed in claim 1, wherein the at least one metabolic substrate is one or more sugars.

16. A liquid culture medium for detecting coagulase-positive staphylococci, comprising:
    peptones;
    at least one sugar capable of being degraded by a metabolic activity of the coagulase-positive staphylococci;
    a fluorescent pH indicator for detecting pH variation of the medium;
    selective agents that permit the growth of the coagulase-positive staphylococci under culture conditions when present in a sample contacted with the medium; and
    D-alanine in an amount from 0.5 mol/L to 1 mol/L in the liquid culture medium.

17. The culture medium as claimed in claim 16, wherein the amount of D-alanine is from 0.05 mol/L to 0.1 mol/L.

18. The culture medium as claimed in claim 16, further comprising growth supplements and a buffer system.

19. A method for determining whether coagulase-positive staphylococci are in a sample, comprising:
    inoculating the liquid culture medium as claimed in claim 16 with the sample;
    incubating the inoculated culture medium under conditions suitable for growth of the coagulase-positive staphylococci; and
    detecting whether the coagulase-positive staphylococci are present in the culture medium in order to determine whether the coagulase-positive staphylococci were present in the sample.

20. The method as claimed in claim 19, further comprising forming the liquid culture medium, before inoculation, using a solution including D-alanine.

* * * * *